(12) United States Patent
Scholz (10) Patent No.: US 7,660,379 B2
(45) Date of Patent: Feb. 9, 2010

(54) METHOD FOR CORRECTING TRUNCATION ARTIFACTS IN A RECONSTRUCTION METHOD FOR COMPUTER TOMOGRAPHY RECORDINGS

(75) Inventor: Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 228 days.

(21) Appl. No.: 12/004,363

(22) Filed: Dec. 20, 2007

(65) Prior Publication Data

US 2008/0165918 A1      Jul. 10, 2008

(30) Foreign Application Priority Data

Dec. 22, 2006    (DE)    ............... 10 2006 062 277

(51) Int. Cl.
*A61B 6/03*       (2006.01)
(52) U.S. Cl. ................................. 378/4; 378/18
(58) Field of Classification Search ............. 378/4, 378/18
See application file for complete search history.

(56) References Cited

U.S. PATENT DOCUMENTS

| 6,307,909 | B1 * | 10/2001 | Flohr et al. | ............... | 378/4 |
| 7,254,259 | B2 * | 8/2007 | Hsieh et al. | ............... | 382/131 |
| 2002/0186809 | A1 * | 12/2002 | Flohr et al. | ............... | 378/4 |
| 2004/0066909 | A1 * | 4/2004 | Lonn et al. | ............... | 378/901 |
| 2008/0123806 | A1 * | 5/2008 | Scholz | ............... | 378/18 |

OTHER PUBLICATIONS

Beyer et al., Whole-Body 18F-FDG PET/CT in the Presence of Truncation Artifacts, Jan. 2006, The Journal of Nuclear Medicine, vol. 47, No. 1, pp. 91-99.*
You et al., FBP algorithms for attenuated fan-beam projections, May 13, 2005, Inverse Problems, vol. 21, pp. 1179-1192.*
Zellerhoff et al., Low contrast 3D-reconstruction from C-arm data, Published online Aug. 30, 2005, SPIE vol. 5745, pp. 646-655.*
Scholtz et al., Correction of Truncation Artifacts in C-arm CT Images by Fan-Beam Extrapolation Using Savitzky-Golay Filter, Dec. 2, 2008, RSNA 2008, Presentation Code: SSJ24-06.*
You, ReconAnalytical Class Reference, Copyright 2003-2005, available at http://www.cubic-imaging.com/CodeDoc/ImageRecon/class_recon_analytical.html.*
Lascu et al., Electrocardiogram Compression and Optimal ECG Filtering Algorithms, Apr. 2008, WSEA Transactions on Computers, Issue 4, vol. 7, pp. 155-164.*

(Continued)

*Primary Examiner*—Edward J Glick
*Assistant Examiner*—John M Corbett (57) ABSTRACT

The invention relates to a method for correcting truncation artifacts in reconstructing computer tomography recordings. The projection images of the computer tomography recordings are extended by extrapolation. An equivalent body is determined which in the peripheral region of the projection image attenuates the radiation emanating from a radiation source of the computer tomography according to the object to be examined, and the attenuation is determined outside the projection image for extrapolated image points. A smoothing of the signal of a projection data line is effected with a digital polynomial filter to reduce the noise portion of the signal. The truncated portion of the projection data line is computed from the smoothed signal of the projection data line by an extrapolation method.

16 Claims, 6 Drawing Sheets

OTHER PUBLICATIONS

Press et al., Numerical Recipes in C. The Art of scientific Computing, 2002, Second Edition, Second Edition, ISBN 0-512-43108-5, Chapter 14.8 Savitzky-Golay Smoothing Filters, pp. 650-655.*

Savitzky et al., Smoothing and Differentiation of Data by Simplified Least Squares Procedures, Jul. 1964, Analytical Chemistry, vol. 36, No. 8, pp. 1627-1639.*

B. Ohnesorge et al., "Efficient correction for CT image artifacts caused by objects extending outside the scan field of view", Med. Phys. 27, vol. 1, , 2000, pp. 39 to 46.

K. Sourbelle et al., "Reconstruction from Truncated Projections in Cone-Beam CT using Adaptive Detruncation", Paper #1506, RSNA 2003, pp. 1-3.

C. Penβel, "Hybrid Detruncation Algorithm for the Reconstruction of CT Data", RSNA paper 2005, pp. 1-18.

J. Hsieh et al., "A novel reconstruction algorithm to extend the CT scan field-of-view", Med. Phys. 31 (9), Sep. 2004, pp. 2385 to 2391.

J. Starman et al., "Extrapolating Truncated Projections Using 0th and 1st Moment Constraints", RSNA 2004, and B. Scholz, Scientific Papers, pp. 1-2.

B. Scholz, "Verfahren zur Korrektur von Trunkierungsartefakten[Method for correcting truncation artifacts]", earlier patent application 10 2006 014 629.8, Mar. 29, 2006.

A. Savitzky et al., "Smoothing and differentiation of data by simplified least squares procedures", Anal. Chem. vol. 36, Jul. 1964, pp. 1627-1639.

* cited by examiner

METHOD FOR CORRECTING TRUNCATION ARTIFACTS IN A RECONSTRUCTION METHOD FOR COMPUTER TOMOGRAPHY RECORDINGS

CROSS REFERENCE TO RELATED APPLICATIONS

This application claims priority of German application No. 10 2006 062 277.4 filed Dec. 22, 2006, which is incorporated by reference herein in its entirety.

FIELD OF THE INVENTION

The invention relates to a method for correcting truncation artifacts in a reconstruction method for computer tomography recordings with truncated projection data in the reconstructed computer tomography images.

BACKGROUND OF THE INVENTION

In computer tomography recordings, it can arise that the object to be imaged exceeds the field-of-measurement area, as will be described below in relation to FIG. 1, in which the measurement geometry and the measurement object which result in cut-off projection data are represented. A cone-beam phantom can be used as a measurement object.

This measured projection data, called cut-off or truncated projection data, generates artifacts in the reconstructed CT images. A profile section through an axial image plane runs in the shape of a dish. Consequently, the CT values close to the image edge are clearly too high. As a rule, the CT values in the image center are also not reconstructed correctly. Such CT images are therefore scarcely usable for diagnostic purposes.

While the known solution methods explained below are capable of reducing the so-called truncation artifacts, residual artifacts can nonetheless on closer inspection still be seen.

The aim of reducing or of eliminating truncation artifacts has predominantly been tackled in the literature by completing the cut-off data so as to obtain in this manner the projection profile which would be produced if the field-of-measurement area had captured the entire object. The completion is carried out by extrapolating the cut-off data line. The type of extrapolation differentiates between the following solution approaches discussed in the literature:

B. Ohnesorge et al. [1] describe in "Efficient correction for CT image artifacts caused by objects extending outside the scan field of view", Med. Phys. 27, Vol. 1, pages 39 to 46, 2000, extrapolation by means of antisymmetrical reflection.

In "Reconstruction from Truncated Projections in Cone-Beam CT using Adaptive Detruncation", Paper #1506, RSNA 2003, by K. Sourbelle et al. [2], a method of correction of exceeding of the field of measurement is described in which the truncated projection data is supplemented as consistently as possible. To do this, an extended field of measurement has first to be defined on which the projections can then be continued. In contrast to similar methods implemented by the manufacturers, extended consistency criteria are applied here. The image reconstruction itself takes place on the extended field of measurement and is designed not to discontinue at the edge of the physical field of measurement.

In "Hybrid Detruncation Algorithm for the Reconstruction of CT Data", RSNA paper 2005, C. Penβel et al. [3] combined the ADT algorithm from [2] with an iterative method which also uses the data that can be seen after back-projection outside the actual field of measurement.

An extrapolation method that has been thoroughly tried and tested in practice is the method described in "A novel reconstruction algorithm to extend the CT scan field-of-view", Med. Phys. 31 (9), September 2004, pages 2385 to 2391, by Hsieh et al. [4], by means of which truncation artifacts that occur when the object to be examined extends into areas outside the so-called field of measurement can be suppressed. The projection images which emerge in the process are termed cut-off or truncated. Truncated projection images generate artifacts in the reconstruction of sectional images. In particular, the image values close to the boundary in the sectional images are as a rule too high and those in a central area too low. The sectional images encumbered with truncation artifacts can therefore be used only to a limited extent for diagnostic purposes. In the method it is assumed that the "cut-off" object is imagined to be continued by a circular water cylinder. The height of the cylinder is equal to the height of the detector and the radius and the position of the midpoint of the circle have to be determined from the projection value and the slope of the projection line at the truncation location, i.e. at the location of the last measured value. As a result of the unavoidable noise of the measurement values, the determination of the slope may not be numerically robust and may consequently yield an incorrect value.

The result is the computation of incorrect extrapolation values and, accompanying this, of an incorrect extrapolation distance. Too short an extrapolation distance reduces only imperfectly the dish-shaped profile of a reconstructed axial section. Too large an extrapolation area overcompensates the "dish" and results in a domed profile section. That means that the outer reconstructed areas of the object are in value terms either still excessively high or depressed and in a gray-scale value diagram will appear lighter or darker than the center of the image. A consequence of this is poor HU fidelity at the object edge and—depending on whether over- or under-compensation has occurred—even in the center of the image.

Further such correction methods are known from J. Starman et al. "Extrapolating Truncated Projections Using 0th and 1st Moment Constraints", RSNA 2004, and B. Scholz, "Verfahren zur Korrektur von Trunkierungsartefakten [Method for correcting truncation artifacts]", earlier patent application 10 2006 014 629.8.

SUMMARY OF THE INVENTION

The object of the invention is to bring about a further reduction of these artifacts such that extrapolation of the cut-off data line matches the original as accurately as possible.

This object is achieved in a method comprising the features of the independent claim. Advantageous embodiments and further developments are described in claims dependent thereon.

The object is achieved according to the invention in that
divergent radiation is emitted by a radiation source,
an object to be examined is irradiated with the divergent radiation in different projection directions,
the radiation that has penetrated the object to be examined is detected by a detector, and
projection images recorded by the detector are extended by means of extrapolation, an equivalent body being determined which in the peripheral region of the projection image attenuates the radiation emanating from the radiation source according to the object to be examined, and the attenuation of the radiation caused by the equivalent body also being determined outside the projection image for extrapolated image points, a smoothing of the signal of a projection data line with a digital polynomial filter is effected to reduce the noise portion of the signal, and the truncated portion of the projection data line is computed from the smoothed signal of the projection data line by means of an extrapolation method.

An optimal reconstruction of truncated regions is obtained in the proposed solution of the aforementioned problem by means of a combination of Savitzky-Golay filters, known from A. Savitzky et al. [7], "Smoothing and differentiation of data by simplified least squares procedures", Anal. Chem. 36, 1627-1639, 1964, and an extrapolation method.

Such Savitzky-Golay smoothing filters (also called digital smoothing polynomial filters or least-squares smoothing filters) are used in order to "smooth out" the noise portion of a signal whose noise-free frequency content is large.

Such an extrapolation method may for example be a water-cylinder extrapolation method known from [4] or from [6].

The extrapolation method may be fashioned such that the equivalent body is arranged in the area of the object to be examined and that to determine the extrapolated image points outside the projection image, the attenuation of beams proceeding from the radiation source to the image points, which occurs upon penetration through the equivalent body, is determined.

BRIEF DESCRIPTION OF THE DRAWINGS

The invention is explained in detail below with the aid of exemplary embodiments represented in the drawings, in which:

FIG. 7 shows intensity curves appertaining to FIGS. 4 to 6, FIGS. 8 to 10 show image results from recordings with a small detector, which have been reconstructed according to different methods.

DETAILED DESCRIPTION OF THE INVENTION

Figure 1:
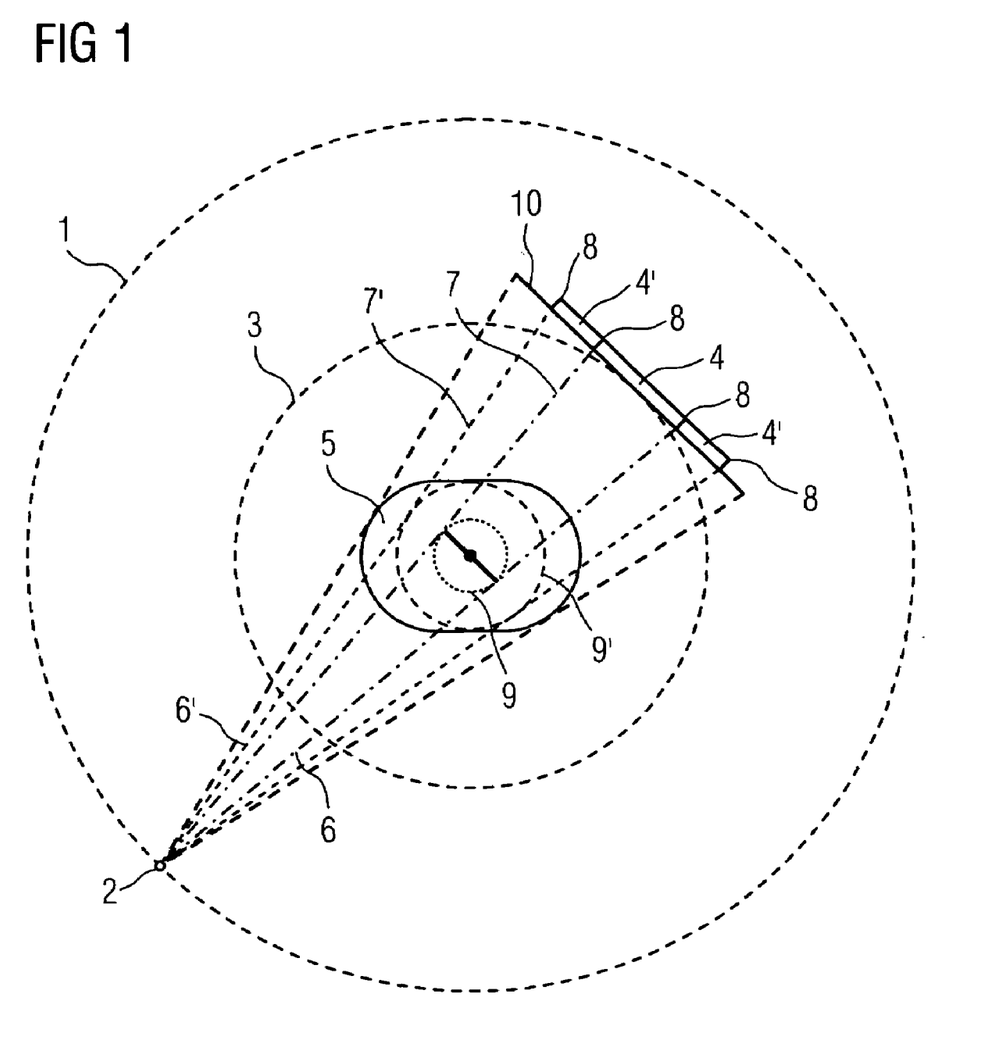
FIG. 1 shows a view of the measurement geometry with the path of a detector and of a radiation source about a measurement object to be examined, viewed in an axial direction.

FIG. 1 shows a view in an axial direction of an orbital path 1 of an x-ray radiation source 2 and of an orbital path 3 of a small x-ray detector 4 or of a large x-ray detector 4' about an object 5 to be examined. The x-ray detector 4 or 4' is preferably a digital flat-screen detector or planar detector.

The small x-ray detector 4 may for example have the dimensions 17.5×17.5 cm² and the large x-ray detector 4' be 29.5×36.0 cm² in size. The object 5 to be examined may, for example, be an animal or human body, but also a phantom body which may, for example, have a height of 26 cm and a width of 37 cm.

The x-ray radiation source 2 emits a beam fan 6 or 6', emanating from a beam focus, the peripheral beams 7 or 7' of which strike edges 8 of the x-ray detector 4 or 4'.

The x-ray radiation source 2 and the x-ray detector 4 or 4' each orbit about the object 5 such that the x-ray radiation source 2 and the x-ray detector 4 or 4' lie opposite one another on opposite sides of the object 5. During the joint movement of x-ray detector 4 or 4' and x-ray radiation source 2, the peripheral beams 7 or 7' of the beam fan 6 define a field-of-measurement circle 9 or 9' which lies partially, where the object 5 has too great an extension, or else wholly inside the object 5 to be examined. The field-of-measurement circle 9 of the small detector may have a diameter Ø=11.7 cm and the field-of-measurement circle 9' of the large detector a diameter Ø=24.0 cm.

The areas of the object 5 lying outside the field-of-measurement circle 9 or 9' are not therefore imaged on the x-ray detector 4 or 4'. Consequently, truncated projection images of the object 5 may possibly be recorded by the x-ray detector 4 or 4'. Sectional images of the object 5 to be examined are reconstructed from the truncated projection images by an evaluation unit (not shown in the drawings), which is connected downstream of the x-ray detector 4 or 4'. The truncated projection images lead to truncation artifacts in the reconstruction of sectional images, lying in the plane of the beam fan 6 or 6', of the irradiated object 5. In particular, image values of the reconstructed sectional image are too high in peripheral regions, whereas the image values in the interior of the sectional image are too low. Even if the object 5 to be examined attenuates the beams of the beam fan 6 or 6' emanating from the x-ray radiation source evenly, an image-value profile running across the sectional image therefore has an approximately dish-like shape.

Image values that are too high signify that in the reconstructed sectional image excessive attenuation of the x-ray radiation emitted by the x-ray radiation source 2 is shown by the object 5, whereas image values that are too low show too little attenuation by the object 5.

In order to reduce the occurrence of truncation artifacts in the reconstructed sectional image, the recorded projection image is extrapolated at the edges 8 of the x-ray detector 4 or 4' onto an extended detector surface 10. The reconstruction is then carried out using the enhanced projection image.

If, prior to the reconstruction of truncated objects known from the literature [1] to [6], a filtering, for example with Savitzky-Golay filters arranged in the evaluation unit (not shown), is carried out, truncation artifacts in the reconstructed sectional image can be reduced extremely effectively.

Figure 2:
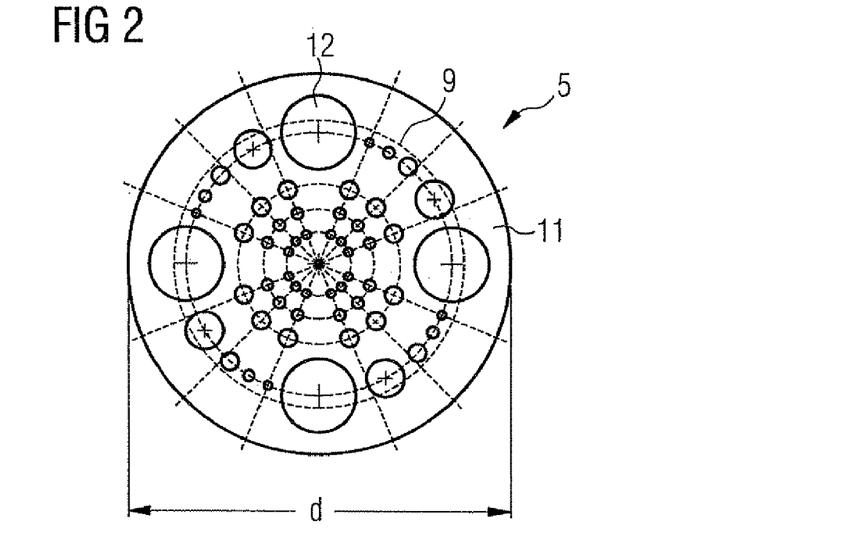
FIG. 2 shows a cross-sectional view of a phantom body used for checking the imaging quality, viewed in an axial direction.

The diagram of the object 5 shown in FIG. 2 is a cross-section through a phantom body 11, which can be used for investigating computer tomography devices. The phantom body 11 has three different contrast layers, each having inserts 12 of different density. A low-contrast layer has inserts 12 with the values 3 HU, 5 HU, 10 HU and 15 HU. A medium-contrast layer has inserts 12 with densities of 20 HU, 25 HU, 30 HU and 40 HU. The external diameter d of the phantom body 11 is dimensioned such that the outer inserts 12 lie partially outside the field-of-measurement circle 9 or 9'.

Figure 3:
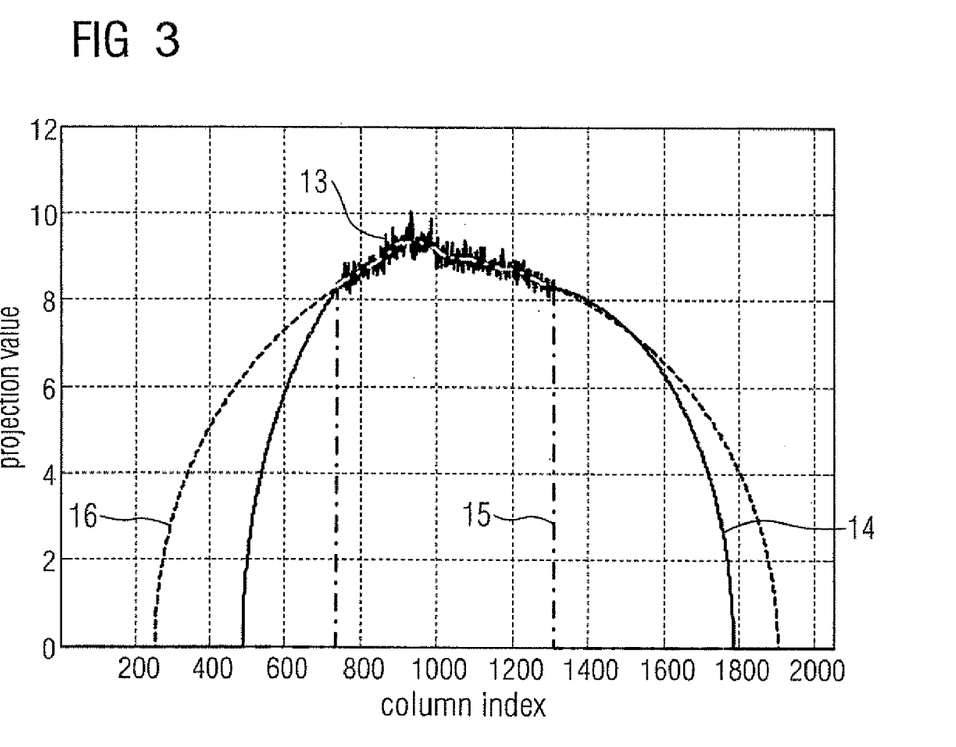
FIG. 3 shows a comparison of the measurement data and of the extrapolation according to the prior art with the corresponding curve forms according to the invention.

FIG. 3 shows the measurement data 13 with a high noise portion and the previous extrapolation curve 14 (here: water-cylinder extrapolation for parallel beams). From the noise-affected measurement data 13, the Savitzky-Golay filtering generates the curve 15, with the aid of which the anticipated extrapolated trace of the curve can clearly be seen. The curve 16 reproduces the fan-beam-based water-cylinder extrapolation curve obtained by means of the Savitzky-Golay curve.

Image results are shown below which have been generated with the product method for eliminating truncation artifacts, with the reconstruction method according to fan-beam-based water-cylinder extrapolation and with the inventive reconstruction method using Savitzky-Golay filtering and fan-beam-based water-cylinder extrapolation. The image results show using C-arm CT data the superiority of the proposed method.

Figure 4:
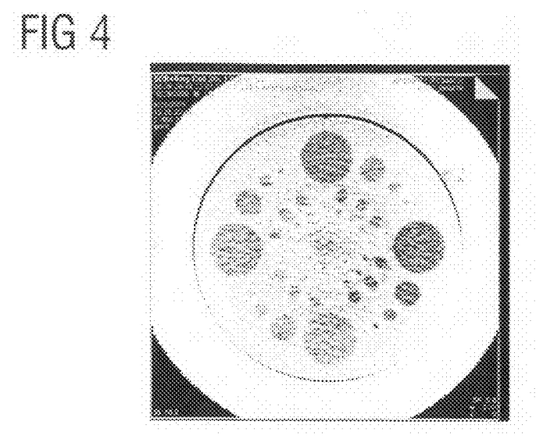
FIGS. 4 to 6 show image results from recordings with a large detector, which have been reconstructed according to different methods.
Figure 5:
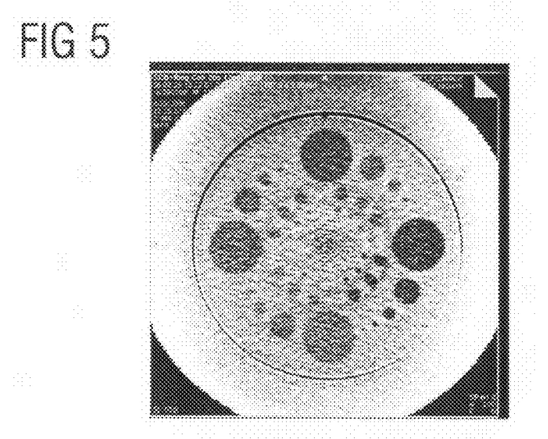
Figure 6:
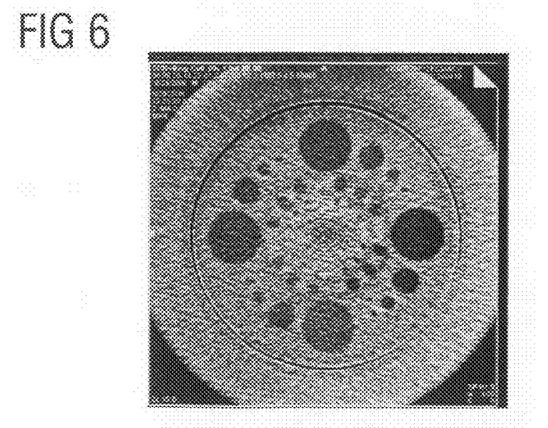

In FIGS. 4 to 6, the recordings have been carried out with the large detector 4'.

FIG. 4 shows the truncated medium-contrast layer of the cone-beam phantom 5 with a reconstruction using up-to-date product software, i.e. for example, a water-cylinder extrapolation according to [4]. The window setting is C/W=0/100, where C=gray-scale value center and W=gray-scale value window width.

FIG. 5 shows the truncated medium-contrast layer of the cone-beam phantom 5, in which a reconstruction has been carried out as per fan-beam-based water-cylinder extrapolation (C/W: 960/200).

FIG. 6 shows the truncated medium-contrast layer of the cone-beam phantom 5, the reconstruction having been carried out using the inventive method (C/W: 0/100).

The improvement in the visual range of the reconstructed layer can be seen clearly in these successive diagrams. The entire range is shown only in the reconstruction according to the invention as per FIG. 6.

Figure 7:
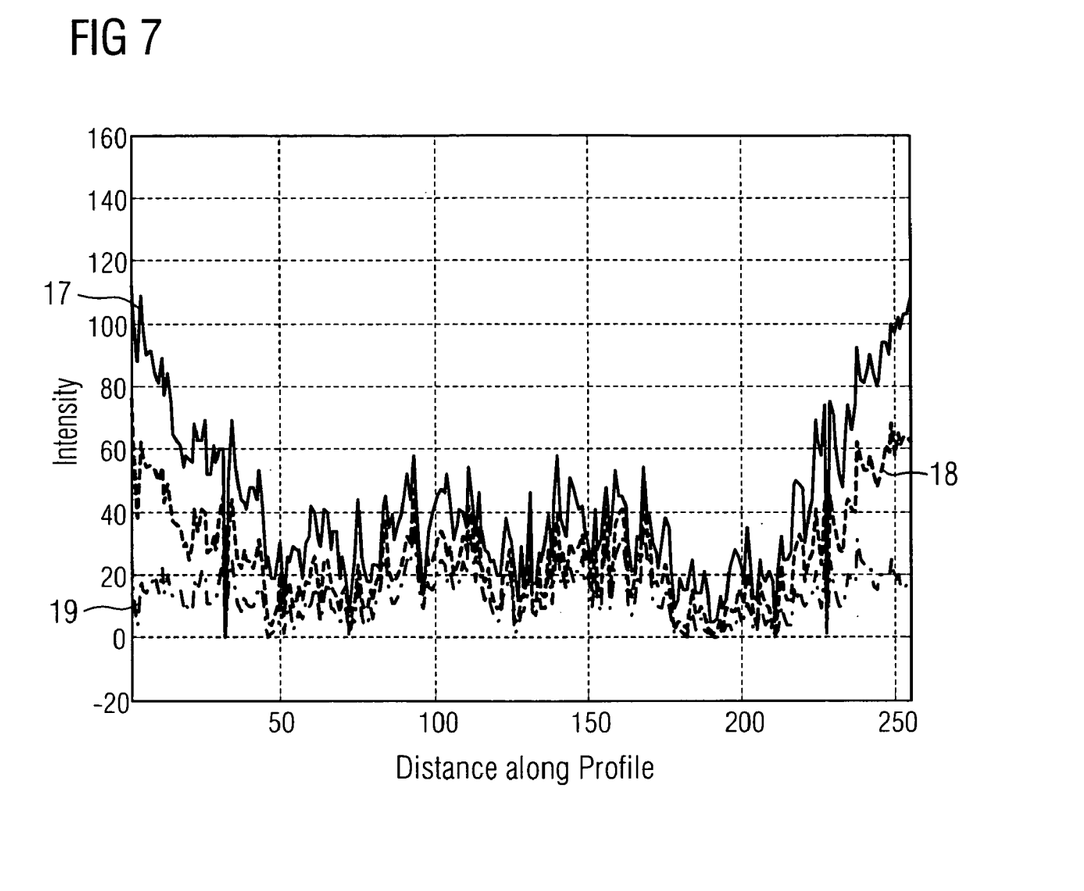

FIG. 7 shows horizontal profile sections through the centers of FIGS. 4 to 6 of the truncated medium-contrast layer of the cone-beam phantom 5, which show the improvements clearly. The level of intensity is plotted over the path of the profile. The signal form 17 in a profile section according to FIG. 4 exhibits sharp banks at the edge. These are already considerably less marked in a signal form 18 in a profile section according to FIG. 5 and absent completely in a signal form 19 of a profile section according to FIG. 6.

Figure 8:
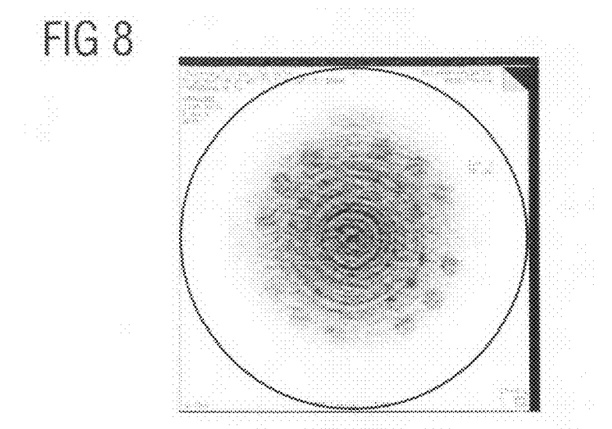
Figure 9:
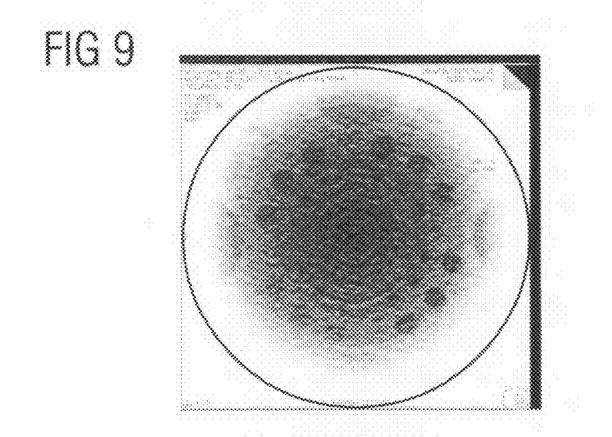
Figure 10:
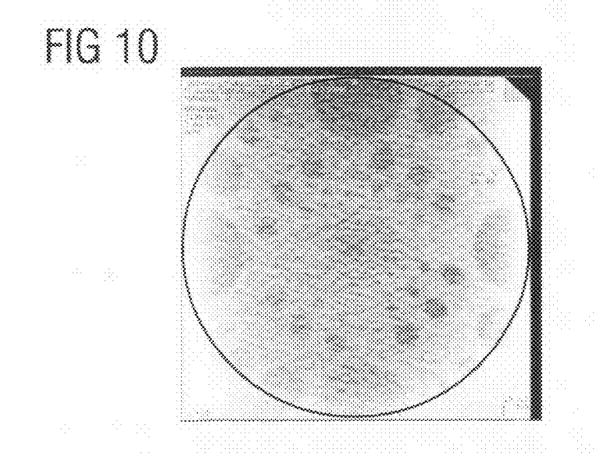

In FIGS. 8 to 10, the recordings have been carried out using the small detector 4, and in these the effects of the inventive reconstruction method can be seen much more clearly.

FIG. 8 shows the truncated medium-contrast layer of the cone-beam phantom with reconstruction using up-to-date product software, i.e. water-cylinder extrapolation according to [4]. The window setting is C/W=300/300.

Represented in FIG. 9 is the truncated medium-contrast layer of the cone-beam phantom by means of reconstruction using fan-beam-based water-cylinder extrapolation (C/W: 300/300).

FIG. 10 shows the truncated medium-contrast layer of the cone-beam phantom according to the reconstruction method according to the invention (C/W: 0/300).

An improvement can clearly be seen here also, although due to the increased truncation the result is not as good as in the corresponding FIG. 6 for the large detector 4'.

Figure 11:
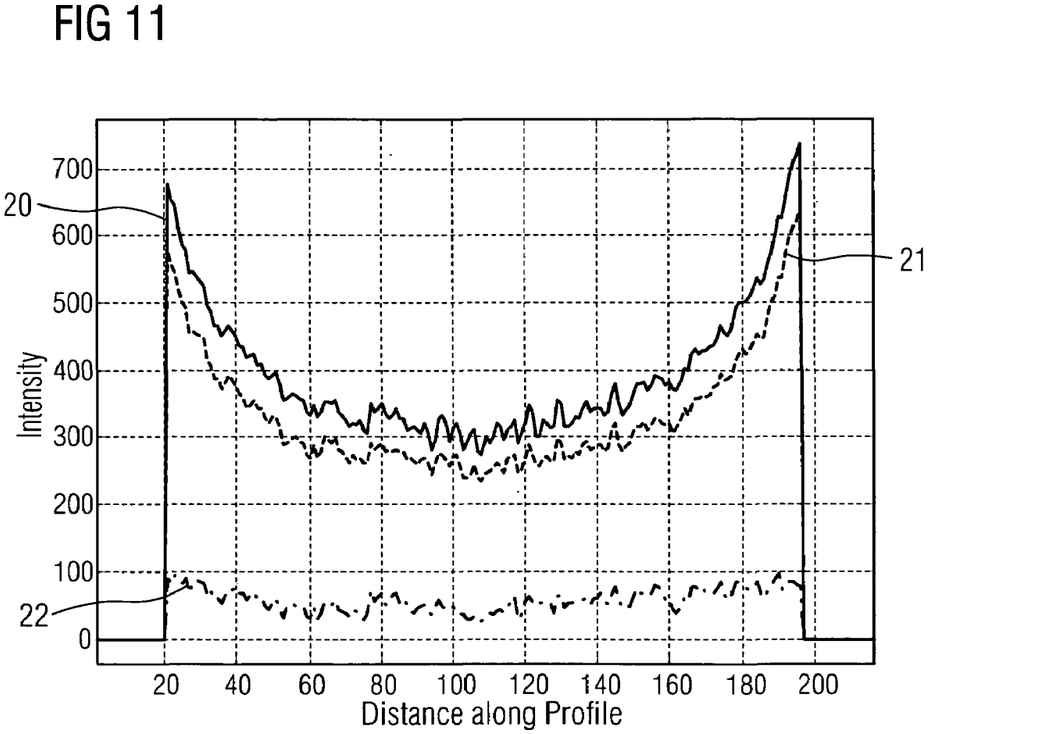
FIG. 11 shows intensity curves appertaining to FIGS. 8 to 10.

FIG. 11 shows the intensities of the truncated medium-contrast layer of the cone-beam phantom in horizontal profile sections through the centers of FIGS. 7 to 9. Here, too, the signal forms 20 in a profile section according to FIGS. 8 and 21 in a profile section according to FIG. 9 exhibit sharp banks at the edge. These banks are, however, completely absent again in a signal form 22 of a profile section according to FIG. 10.

Excellent extrapolated truncation correction for CT-type reconstructions is obtained by the method according to the invention using Savitzky-Golay filters.

By means of the Savitzky-Golay smoothing of a projection data line, a profile is generated whose slope most closely corresponds to the slope of a noise-free signal and consequently allows robust computation of the slopes at the truncation locations. The result is a smooth extrapolation of the cut-off line even in cases of intense noise and consequently a more realistic and more reliable determination of the extrapolation region.

The invention claimed is:

1. A method for correcting a truncation artifact in reconstructing computer tomography recordings, comprising:
   emitting a divergent radiation by a radiation source;
   irradiating an object to be examined with the divergent radiation in a plurality of different projection directions;
   recording a plurality of projection images of the object by detecting the divergent radiation penetrated the object;
   extending the projection images by extrapolation;
   smoothing projection data of the projection images with a digital smoothing polynomial filter to reduce a noise portion of the projection data; and
   computing a truncated portion of the projection data from the smoothed projection data.

2. The method as claimed in claim 1, wherein the digital smoothing polynomial filter is a least-squares smoothing filter.

3. The method as claimed in claim 1, wherein the digital smoothing polynomial filter is a Savitzky-Golay smoothing filter.

4. The method as claimed in claim 1, wherein the truncated portion of the projection data is computed from the smoothed projection data by an extrapolation method.

5. The method as claimed in claim 4, wherein the extrapolation method is a water-cylinder extrapolation method.

6. The method as claimed in claim 1, wherein an equivalent body is determined for extending the projection images.

7. The method as claimed in claim 6, wherein the equivalent body attenuates the divergent radiation in a peripheral region of the projection images and the attenuation is determined for extrapolated image points outside the projection images.

8. The method as claimed in claim 7, wherein the equivalent body is arranged in a region of the object.

9. A medical system for correcting a truncation artifact in reconstructing computer tomography recordings, comprising:
   a computer tomography device that records a plurality of projection images of an object to be examined; and
   an imaging processing device that:
      extends the projection images by extrapolation,
      smoothes projection data of the projection images with a digital smoothing polynomial filter to reduce a noise portion of the projection data, and
      computes a truncated portion of the projection data from the smoothed projection data by an extrapolation method.

10. The medical system as claimed in claim 9, wherein the digital smoothing polynomial filter is a least-squares smoothing filter.

11. The medical system as claimed in claim 9, wherein the digital smoothing polynomial filter is a Savitzky-Golay smoothing filter.

12. The medical system as claimed in claim 9, wherein the truncated portion of the projection data is computed from the smoothed projection data by an extrapolation method.

13. The medical system as claimed in claim 12, wherein the extrapolation method is a water-cylinder extrapolation method.

14. The medical system as claimed in claim 9, wherein an equivalent body is determined for extending the projection images.

15. The medical system as claimed in claim 14, wherein the equivalent body attenuates the divergent radiation in a peripheral region of the projection images and the attenuation is determined for extrapolated image points outside the projection images.

16. The medical system as claimed in claim 15, wherein the equivalent body is arranged in a region of the object.

* * * * *